United States Patent
Notte et al.

(10) Patent No.: US 7,884,248 B2
(45) Date of Patent: Feb. 8, 2011

(54) PROCESS FOR THE MANUFACTURE OF AMINOPOLYALKYLENEPHOSPHONIC ACID COMPOUNDS

(75) Inventors: Patrick P. Notte, Wavre (BE); Isabelle Emmanuel Vanesse, Chastre-Villeroux (BE); Jan H. J. Van Bree, Ottenburg (BE)

(73) Assignee: Thermphos Trading GmbH, Zug (CH)

( * ) Notice: Subject to any disclaimer, the term of this patent is extended or adjusted under 35 U.S.C. 154(b) by 0 days.

(21) Appl. No.: 11/814,107

(22) PCT Filed: Nov. 7, 2005

(86) PCT No.: PCT/EP2005/011967

§ 371 (c)(1),
(2), (4) Date: Jul. 17, 2007

(87) PCT Pub. No.: WO2006/074729

PCT Pub. Date: Jul. 20, 2006

(65) Prior Publication Data

US 2008/0234519 A1    Sep. 25, 2008

(30) Foreign Application Priority Data

Jan. 17, 2005  (EP) .................................. 05447002

(51) Int. Cl.
*C07F 9/02*   (2006.01)

(52) U.S. Cl. ......................................................... 568/14
(58) Field of Classification Search .................... 562/16, 562/17; 564/15
See application file for complete search history.

(56) References Cited

U.S. PATENT DOCUMENTS

| 3,459,793 A | 8/1969 | Shen et al. |
| 5,688,994 A * | 11/1997 | Baysdon et al. ................ 562/17 |
| 6,232,494 B1 * | 5/2001 | Morgenstern et al. ......... 562/17 |

FOREIGN PATENT DOCUMENTS

| FR | 1342412 A | 11/1962 |
| JP | 57075990 | * 5/1982 |
| JP | 57075990 A | 5/1982 |

OTHER PUBLICATIONS

Moedritzer et al., The Direct Synthesis of Alpha-Aminomethylphosphonic Acids, Mannich-Type Reactions with Orthophosphorous Acid, Journal of Organic Chemistry, American Chemical Society, Easton, US, vol. 31, May 1966, pp. 1603-1607.

Tramontiti et al., Further Advances in the Chemistry of Mannich Bases, Tetrahedron, Elsevier Science Publishers, Amsterdam, NL, vol. 46, No. 6, 1990, pp. 1791-1837.

* cited by examiner

*Primary Examiner*—Daniel M Sullivan
*Assistant Examiner*—Chukwuma O Nwaonicha
(74) *Attorney, Agent, or Firm*—Husch Blackwell LLP

(57) ABSTRACT

A beneficial method for the manufacture of amino polyalkylene phosphonic acids, under substantial absence of hydrohalogenic acid, is disclosed. The method, in essence, is based on reacting narrowly defined ratios of phosphorous acid, an amine, a formaldehyde in presence of specific ranges of an acid catalyst having a pKa equal or inferior to 3.1. The inventive method is capable of yielding economically and quality operational/capacity advantages, in particular significantly reduced one-step cycle duration under exclusion, of corrosion disadvantages and also is environmentally friendly without requiring, in that respect, anything more than nominal capital expenditures.

21 Claims, No Drawings

PROCESS FOR THE MANUFACTURE OF AMINOPOLYALKYLENEPHOSPHONIC ACID COMPOUNDS

CROSS REFERENCE TO RELATED APPLICATIONS

This application is a U.S. National Phase Application of International Application PCT Application No. PCT/EP2005/011967 filed on Nov. 7, 2005, which claims the benefit of priority from European Patent Application No. 05447002.6 filed on Jan. 17, 2005. The disclosures of International Application PCT Application No. PCT/EP2005/011967 and European Patent Application No. 05447002.6 are incorporated herein by reference.

This invention relates to a method for the manufacture of aminopolyalkylene phosphonic acid compounds, in particular compounds wherein all the available N—H functions in a majority of the amine or ammonia raw material, have been alkylene phosphonated, under substantial exclusion of hydrohalogenic acid, byproducts and intermediates. In more detail, aminopolyalkylene phosphonic acid compounds can be manufactured beneficially by reacting narrowly defined ratios of: phosphorous acid, an amine, and formaldehyde, in the presence of an acid catalyst having a pKa equal to or smaller than 3.1 with the proviso that the acid catalyst can be homogeneously incorporated into the reaction medium.

Aminoalkylene phosphonic acid compounds are generally old in the art and have found widespread commercial acceptance for a variety of applications including water-treatment, scale-inhibition, detergent additives, sequestrants, marine-oil drilling adjuvants and as pharmaceutical components. It is well known that such industrial applications preferably require amino alkylene phosphonic acids wherein a majority of the N—H functions of the ammonia/amine raw material have been converted into the corresponding alkylene phosphonic acid. The art is thus, as one can expect, crowded and is possessed of methods for the manufacture of such compounds. The state-of-the-art manufacture of amino alkylene phosphonic acids is premised on converting phosphorous acid resulting from the hydrolysis of phosphorus trichloride or on converting phosphorous acid via the addition of hydrochloric acid which hydrochloric acid can be, in part or in total, added in the form of an amine hydrochloride.

The manufacture of amino alkylene phosphonic acids is described in GB 1.142.294. This art is premised on the exclusive use of phosphorus trihalides, usually phosphorus trichloride, as the source of the phosphorous acid reactant. The reaction actually requires the presence of substantial quantities of water, frequently up to 7 moles per mole of phosphorus trihalide. The water serves for the hydrolysis of the phosphorus trichloride to thus yield phosphorous and hydrochloric acids. Formaldehyde losses occur during the reaction which is carried out at mild temperatures in the range of from 30-60° C. followed by a short heating step at 100-120° C. GB 1.230.121 describes an improvement of the technology of GB 1.142.294 in that the alkylene polyaminomethylene phosphonic acid may be made in a one-stage process by employing phosphorus trihalide instead of phosphorous acid to thus secure economic savings. The synthesis of aminomethylene phosphonic acids is described by Moedritzer and Irani, J. Org. Chem., Vol 31, pages 1603-1607 (1966). Mannich-type reactions, and other academic reaction mechanisms, are actually disclosed. Optimum Mannich conditions require low-pH values such as resulting from the use of 2-3 moles of concentrated hydrochloric acid/mole of amine hydrochloride. The formaldehyde component is added dropwise, at reflux temperature, to the reactant solution mixture of aminohydrochloride, phosphorous acid and concentrated hydrochloric acid. U.S. Pat. No. 3,288,846 also describes a process for preparing aminoalkylene phosphonic acids by forming an aqueous mixture, having a pH below 4, containing an amine, an organic carbonyl compound e.g. an aldehyde or a ketone, and heating the mixture to a temperature above 70° C. whereby the amino alkylene phosphonic acid is formed. The reaction is conducted in the presence of halide ions to thus inhibit the oxidation of orthophosphorous acid to orthophosphoric acid. WO 96/40698 concerns the manufacture of N-phosphonomethyliminodiacetic acid by simultaneously infusing into a reaction mixture water, iminodiacetic acid, formaldehyde, a source of phosphorous acid and a strong acid. The source of phosphorous acid and strong acid are represented by phosphorus trichloride.

The use of phosphorus trichloride for preparing aminopolyalkylene phosphonic acids is, in addition, illustrated and emphasized by multiple authors such as Long et al. and Tang et al. in Huaxue Yu Nianhe, 1993 (1), 27-9 and 1993 34(3), 111-14 respectively. Comparable technology is also known from Hungarian patent application 36825 and Hungarian patent 199488. EP 125766 similarly describes the synthesis of such compounds in the presence of hydrochloric acid; along the same lines, JP 57075990 recommends preparing such compounds starting from phosphorous acid by reacting it with an amine in the presence of concentrated hydrochloric acid.

JP patent application 57075990 describes a method for the manufacture of diaminoalkane tetra(phosphonomethyl) by reacting formaldehyde with diaminoalkane and phosphorous acid in the presence of a major level of concentrated hydrochloric acid.

It is a main object of this invention to provide a method for the manufacture of amino polyalkylene phosphonic acid (AAP) under substantial absence of hydrohalogenic, in particular hydrochloric acid, byproducts and intermediates therefrom. Another object of the invention concerns the manufacture of aminoalkylene phosphonic acids starting from ammonia or amine raw materials whereby all the available N—H functions are predominantly converted into the corresponding alkylene phosphonic acid derivatives. In particular, all the N—H functions in 50% or more of the amine/ammonia raw material are reacted to yield alkylene phosphonic acid derivatives. Not more than 60%, preferably not more than 40% of the reacted amine raw material, expressed in relation to the amine raw material wherein all the N—H functions have been converted into alkylene phosphonic acid (100%), carry at least one N—H function that has not been converted into an alkylene phosphonic acid derivative. It is another object of this invention to more efficiently use, during the manufacture of AAP, the formaldehyde reactant which can suffer from the presence of hydrohalogenic acid in the formaldehyde distillate. It is a further object of this invention to provide a process for the manufacture of AAP thereby minimizing the oxidation of phosphorous acid to phosphoric acid. Yet another object of this inventions aims at producing AAP thereby substantially completely eliminating the release to the atmosphere, or the abatement by e.g. thermal oxidation, of environmentally less desirable byproducts such as methylchloride. Another object of this invention aims at generating AAP manufacturing technology, which is not affected by substantial corrosion problems. Yet another object of this invention aims at providing efficient, non-capital intensive, AAP manufacturing technology. Still another object of this invention aims at generating acid catalysts for the manufacture of AAP under substantial absence of hydrohalogenic acids or precursors therefore. The foregoing and other objects can now be met by means of the inventive technology herein as follows.

The "percentage" or "%" indications hereinafter stand, unless defined differently, for "percent by weight". The terms "phosphonic acid" and "phosphonate" can be used, throughout the description and claims, interchangeably. The term "poly" in "aminopolyalkylene phosphonic acid" means that at least two alkylene phosphonic acid moieties are present in the compound. The reactant designation "phosphorous acid" embraces the individual reactant per sé and the precursors therefore. The term "amine" embraces amines per sé and ammonia. The term "formaldehyde" designates interchangeably formaldehyde, sensu stricto, aldehydes and ketones.

It has now been discovered that aminopolyalkylene phosphonic acid compounds can be manufactured beneficially, in the presence of not more than 0.4%, expressed in relation to the phosphorous acid component (100%), of hydrohalogenic acid, whereby all the available N—H functions in 50% or more of the amine raw material are converted to the corresponding alkylene phosphonic acids, by reacting:

(a): phosphorous acid;
(b): an amine; and
(c): a formaldehyde;

in reactant ratios as follows:

(c):(a) of from 5:1 to 0.25:1;
(a):(b) of from 0.05:1 to 2:1; and
(c):(b) of from 0.05:1 to 5:1;

wherein (a) and (c) stand for the number of moles to be used and (b) represents the number of moles multiplied by the number of N—H functions in the amine, in the presence of an acid catalyst having a pKa equal or inferior to 3.1, said acid catalyst (d) being homogeneous with respect to the reaction medium and being used in reactant ratios as follows:

(b):(d) of from 40:1 to 1:5;

wherein (d) stands for the number of moles of catalyst multiplied by the number of available protons per mole of catalyst, followed by recovering the amino polyalkylene phosphonic acid formed in a manner known per sé.

In preferred executions herein the reactant ratios are as follows:

(a):(b) of from 0.1:1 to 1.5:1,
(c):(b) of from 0.2:1 to 2:1, and
(c):(a) of from 3:1 to 0.5:1.

In particularly useful executions the reactant ratios are narrowly defined as follows;

(a):(b) of from 0.4:1 to 1.0:1.0,
(c):(b) of from 0.4:1 to 1.5:1, and
(c):(a) of from 2:1 to 1.0:1.

The phosphorous acid component can be used as such or can be entered in its P-oxide form. Phosphorous acid and the corresponding P-oxides can be derived from any suitable precursor including naturally occurring phosphorus containing rocks which can be converted, in a known manner, to elemental phosphorus followed by oxidation to P-oxides and possibly phosphorous acid. The phosphorous acid reactant can also be prepared, starting from hydrolyzing $PCl_3$ and purifying the phosphorous acid so obtained by eliminating hydrochloric acid and other chloride intermediates originating from the hydrolysis.

The method herein is conducted in the presence of not more than 0.4%, preferably 2000 parts-per-million (ppm) or less, more preferably 200 ppm or less, expressed in relation to the phosphorous acid component (100%), of hydrochloric acid.

While the preparation of phosphorous acid by the direct oxidation of elemental phosphorus and hydrolysis of the resulting P-oxides is known to be difficult, various technologies can be economically acceptable in that respect. Canadian patent application 2.070.949 divulges a method for the manufacture of phosphorous acid, or the corresponding $P_2O_3$ oxide, by introducing gaseous phosphorus and steam water into a gas plasma reaction zone at a temperature in the range of 1500° K. to 2500° K. to thus effect conversion to $P_2O_3$ followed by rapidly quenching the phosphorus oxides at a temperature above 1500° K. with water to a temperature below 1100° K. to thus yield $H_3PO_3$ of good purity. In another approach, phosphorus(I) and (III) oxides can be prepared by catalytic reduction of phosphorus(V) oxides as described in U.S. Pat. No. 6,440,380. The oxides can be hydrolyzed to thus yield phosphorous acid. EP-A-1.008.552 discloses a process for the preparation of phosphorous acid by oxidizing elemental phosphorus in the presence of an alcohol to yield P(III) and P(V) esters followed by selective hydrolysis of the phosphite ester into phosphorous acid. WO 99/43612 describes a catalytic process for the preparation of P(III) oxyacids in high selectivity. The catalytic oxidation of elemental phosphorus to phosphorous oxidation levels is also known from U.S. Pat. Nos. 6,476,256 and 6,238,637.

In another approach, phosphorous acid can be manufactured beneficially by reacting phosphorus trichloride with a reagent which is either a carboxylic acid or a sulfonic acid or an alcohol. The $PCl_3$ reacts with the reagent under formation of phosphorous acid and an acid chloride in the case an acid reagent or a chloride, for example an alkylchloride, originating from the reaction of the $PCl_3$ with the corresponding alcohol. The chlorine containing products, e.g. the alkylchloride and/or the acid chloride, can be conveniently separated from the phosphorous acid by methods known in the art e.g. by distillation. While the phosphorous acid so manufactured can be used as such in the claimed arrangement, it can be desirable and it is frequently preferred to purify the phosphorous acid formed by substantially eliminating or diminishing the levels of chlorine containing products and non-reacted raw materials. Such purifications are well known and fairly standard in the domain of the relevant manufacturing technology. Suitable examples of such technologies include the selective adsorption of the organic impurities on active carbon or the use of aqueous phase separation for the isolation of the phosphorous acid component. Information pertinent to the reaction of phosphorous trichloride with a reagent such as a carboxylic acid or an alcohol can be found in Kirk-Othmer, Encyclopedia of Chemical Technology, in chapter Phosphorous Compounds, Dec. 4, 2000, John Wiley & Sons Inc.

In one preferred execution herein, the phosphorous acid reactant used in the method of the invention is represented by species prepared under substantial exclusion of halogens. Such methods for preparing phosphorous acid under the exclusion of halogens are well known in the domain of the technology. Specific examples of methods which can be used for preparing such phosphorous acid reactants are summarized hereinafter.

In one method (i), phosphorous acid can be prepared by contacting elemental phosphorus, preferably tetraphosphorus, with water, at a temperature below 200° C., in the presence of a catalyst effective to promote oxidation of phosphorus by reaction with water such as a noble metal catalyst e.g. Pd, to thus yield phosphorous acid in high selectivity. This process is described in U.S. Pat. No. 6,238,637 B1. Substantially identical disclosures can be taken from WO 99/43612 and U.S. Pat. No. 6,476,256 B1. In another approach (ii), predominantly P(III) species, such as phosphorous acid, can be prepared by contacting P(V) species with a reducing agent such as hydrogen in the presence of a reducing catalyst. This process is described in detail in U.S. Pat. No. 6,440,380 B1. In yet another process (iii), phosphorous acid can be manufactured by the selective hydrolysis of phosphite esters. A hydrolysis feed mixture comprising phosphite esters and phosphate esters is contacted with liquid water and steam to selectively hydrolyse the phosphite esters to phosphorous acid. EP 1.008.552 A1 provides an enabling description of this technology.

The essential amine component can be represented broadly by conventional nitrogen-containing reactants. More specifically, the amine component can be selected from the group of:

ammonia;

primary and secondary amines containing individual hydrocarbon groups having from 1 to 100, preferably 1 to 50, carbon atoms, said hydrocarbon moieties can be represented by straight or branched linear alkyl moieties or cyclic alkyl moieties or aromatic or polyaromatic moieties or combinations thereof;

polyamines; and primary and secondary amines and polyamines containing alkoxylated or thioalkoxylated radicals and/or functional groups including functionalized silyl groups such as trialkyl silyl, hydroxyl, carboxylic acid or sulfonic acid or esters of such acids or combinations thereof.

Specific examples of alkylamines are methylamine, ethylamine, butyl amine, octyl amine, decyl amine, dodecyl amine, stearyl amine, dimethyl amine, diethyl amine, dibutyl amine, naphthyl amine, benzyl amine, aniline and cyclohexyl amine. Also primary or secondary aliphatic amines containing substituted alkyl groups can be used.

Suitable polyamine species include ethylene diamine, diethylene triamine, triethylene tetramine, di(propylene)ethylene tetramine, di(hexamethylene) triamine, hexamethylene diamine and polymeric amines such as polyethylene imine and polyallylamine.

While the amine may be used in the free form, it is often preferred to use it in the form of a salt, such as a sulfate.

The essential formaldehyde component is a well known commodity ingredient. Formaldehyde sensu stricto known as oxymethylene having the formula $CH_2O$ is produced and sold as water solutions containing variable, frequently minor, e.g. 0.3-3%, amounts of methanol and are typically reported on a 37% formaldehyde basis although different concentrations can be used. Formaldehyde solutions exist as a mixture of oligomers. Such formaldehyde precursors can, for example, be represented by paraformaldehyde, a solid mixture of linear poly(oxymethylene glycols) of usually fairly short, n=8-100, chain length, and cyclic trimers and tetramers of formaldehyde designated by the terms trioxane and tetraoxane respectively.

The formaldehyde component can also be represented by aldehydes and ketones having the formula $R_1R_2C=O$ wherein $R_1$ and $R_2$ can be identical or different and are selected from the group of hydrogen and organic radicals. When $R_1$ is hydrogen, the material is an aldehyde. When both $R_1$ and $R_2$ are organic radicals, the material is a ketone. Species of useful aldehydes are, in addition to formaldehyde, acetaldehyde, caproaldehyde, nicotinealdehyde, crotonaldehyde, glutaraldehyde, p-tolualdehyde, benzaldehyde, naphthaldehyde and 3-aminobenzaldehyde. Suitable ketone species for use herein are acetone, methylethylketone, 2-pentanone, butyrone, acetophenone and 2-acetonyl cyclohexanone.

The technology herein requires the presence of an acid catalyst having a pKa equal or inferior to 3.1, preferably equal or inferior to 2.75, most preferably equal or inferior to 1.9, especially inferior to 1.9, said catalyst being homogeneously compatible with the reaction medium. The pKa value is a well known variable which can be expressed as follows:

$$pKa=-\log_{10}Ka.$$

wherein Ka represents the thermodynamic equilibrium acidity constant.

The pKa values of practically all acid substances are known from the literature or can, if this were needed, be determined conveniently. Homogeneous catalysts are catalysts adapted to form a single liquid phase within the reaction medium under the reaction conditions. It is understood that catalysts which are insoluble or immiscible in the reaction medium, and thus non-homogeneous, at ambient conditions e.g. 20° C., can become miscible or soluble at e.g. the reaction temperature and thus qualify as "homogeneous". The acid catalyst may be recovered from the reaction medium by known techniques such as e.g. filtration of insoluble acids, phase separation of immiscible acids, or by other techniques routinely available such as ion exchange, nanofiltration or electrodialysis. The homogeneous nature of an acid catalyst can be ascertained routinely by e.g. visible inspection of precipitation or phase separation properties.

The acid catalyst is used, in the reaction mixture, in a ratio of: (b):(d) in the range from 40:1 to 1:5, preferably 20:1 to 1:3, most preferably 10:1 to 1:2. In that respect, (b) represents the number of moles of amine multiplied by the number of N—H functions in the amine; and (d) being expressed as the number of moles of acid catalyst multiplied by the number of available protons per mole of catalyst. Suitable species of acid catalyst for use herein can e.g. be represented by sulfuric acid, sulfurous acid, trifluoroacetic acid, trifluoromethane sulfonic acid, methane sulfonic acid, oxalic acid, p-toluene sulfonic acid and naphthalene sulfonic acid. Mixtures of the acid catalyst species can also be used.

The reaction in accordance with this invention is conducted in a manner routinely known in the domain of the technology. As extensively illustrated in the experimental showings, the method can be conducted by combining the essential reactants and heating the reaction mixture to a temperature usually within the range of from 45° C. to 200° C., and higher temperatures if elevated pressures are used, more preferably 70° C. to 150° C. The upper temperature limit actually aims at preventing any substantially undue thermal decomposition of the phosphorous acid reactant. It is understood and well known that the decomposition temperature of the phosphorous acid reactant, and more in general of any other individual reactant, can vary depending upon additional physical parameters, such as pressure and the qualitative and quantitative parameters of the co-reactants in the reaction mixture.

The inventive reaction can be conducted at ambient pressure and, depending upon the reaction temperature, under distillation of water, thereby also eliminating a minimal amount of non-reacted formaldehyde. The duration of the reaction can vary from virtually instantaneous, e.g. 1 minute, to an extended period of e.g. 4 hours. This duration generally includes the gradual addition, during the reaction, of formaldehyde and possibly other reactants. In one method set up, the phosphorous acid, the amine and the acid catalyst are added to the reactor followed by heating this mixture under gradual addition of the formaldehyde component starting at a temperature e.g. in the range of from 70° C. to 150° C. This reaction can be carried out under ambient pressure with or without distillation of usually water and some non-reacted formaldehyde.

In another operational arrangement, the reaction can be conducted in a closed vessel under autogeneous pressure built up. In this method, the reactants, in total or in part, are added to the reaction vessel at the start. In the event of a partial reactant mixture, the additional reactant can be gradually added, alone or with any one or more of the other reactants, as soon as the effective reaction temperature has been reached. The gradual addition of formaldehyde, alone or in admixture with other reactants, during the effective reaction is illustrated in the Examples. The formaldehyde reactant can, for example, be added gradually during the reaction alone or with parts of the amine or the phosphorous acid or the acid catalyst.

In yet another operational sequence, the reaction can be conducted in a combined distillation and pressure arrangement. Specifically, the reaction vessel containing the reactant mixture is kept under ambient pressure at the selected reaction temperature. The mixture is then, possibly continuously, circulated through a reactor operated under autogeneous (autoclave principle) pressure built up thereby gradually adding the formaldehyde or additional reactants in accordance with needs. The reaction is substantially completed under pressure and the reaction mixture then leaves the closed vessel and is recirculated into the reactor where distillation of water and other non-reacted ingredients can occur depending upon the reaction variables, particularly the temperature.

The foregoing process variables thus show that the reaction can be conducted by a variety of substantially complementary arrangements. The reaction can thus be conducted as a batch process by heating the initial reactants, usually the phosphorous acid, the amine and the acid catalyst in a (1) closed vessel under autogeneous pressure built up, or (2) under reflux conditions, or (3) under distillation of water and minimal amounts of non-reacted formaldehyde, to a temperature preferably in the range of from 70° C. to 150° C. whereby the formaldehyde component is added, as illustrated in the Examples, gradually during the reaction. In a particularly preferred embodiment, the reaction is conducted in a closed vessel at a temperature in the range of from 100° C. to 150° C., coinciding particularly with the gradual addition of formaldehyde, within a time duration of from 1 minute to 30 minutes, in a more preferred execution from 1 minute to 10 minutes.

In another approach, the reaction is conducted as a continuous process, possibly under autogeneous pressure, whereby the reactants are continuously injected into the reaction mixture, at a temperature preferably in the range of from 70° C. to 150° C. and the phosphonic acid reaction product is withdrawn on a continuous basis.

In yet another arrangement, the method can be represented by a semi-continuous set-up whereby the phosphonic acid reaction is conducted continuously whereas preliminary reactions between part of the components can be conducted batch-wise.

The inventive technology is illustrated by means of specific examples as follows.

EXAMPLE 1

Aminotrimethylene phosphonic acid (ATMP) was prepared by reacting phosphorous acid, ammonia and formaldehyde in the presence of a methanesulfonic acid catalyst. The individual components were used in the recited proportions.

| Reactant | g | mole (s) |
|---|---|---|
| Phosphorous acid | 100.45 | 1.225 |
| Methanesulfonic acid | 15.43 | 0.161 |
| Ammonia (25% solution) | 27.2 | 0.4 |
| Formaldehyde (36.6% solution) | 103.27 | 1.26 |
| Water | 58.07 | — |

The phosphorous acid was first added to the reactor followed by the water, the methanesulfonic acid and the ammonia. The reaction mixture so prepared was subsequently heated to 105° C. at which temperature the gradual addition of the formaldehyde was started. The formaldehyde was added in a period of 2 hours. The reaction was, after the addition of the formaldehyde, continued under reflux conditions for a further period of 2 hours.

The reaction product was analyzed by means of a 31P-NMR spectroscopic method. It was found that ATMP was formed with a yield of 59.1%.

Additional ATMP preparations were conducted thereby using the method set forth in Example 1 and conducting the reactions in accordance with that Example 1 except that the methanesulfonic acid catalysts were utilized in the following levels.

| Example | g | mole (s) |
|---|---|---|
| 2 | 61.85 | 0.644 |
| 3 | 42.33 | 0.441 |

The reaction product formed, analyzed as described in Example 1, showed a yield of ATMP of

| Example 2 | 76.8 % |
|---|---|
| Example 3 | 72.7 %. |

These Examples (1-3) demonstrate the unexpected benefits of the inventive technology and show that the aminopolymethylene phosphonic acids can be prepared under exclusion of hydrohalogenic reactants in a short cycle time and in high yields as compared to state-of-the-art methods using the $PCl_3$ route. Example 1, in addition to containing 59.1% ATMP, was found to contain 15.9% N-methylimino bis(methylene phosphonic acid) (N-MeIBMPA) and 16.5% phosphorous acid. Example 2 contained, in addition to 76.8% ATMP, 6.8% N-MeIBMPA and 9% phosphorous acid.

Example 3 contained, in addition to a high level of ATMP, 8.3% N-MeIBMPA and 12% phosphorous acid. The one-step reaction was, for all three examples, completed in about 4 hours as compared to a multi-step procedure lasting generally more than 6 hours, starting from phosphorus trichloride.

ATMP samples were prepared thereby using the method in accordance with Example 1, except that the reaction was conducted under continuous distillation at the temperature of the reaction. The individual reactants, except the catalyst and the added water, were used, in Examples 4-8, in identical proportions as follows:

| Reactant | g | mole (s) |
|---|---|---|
| Phosphorous acid | 100.45 | 1.225 |
| Ammonia (25% solution) | 27.2 | 0.4 |
| Formaldehyde (36.6% solution) | 103.27 | 1.26 |

The methanesulfonic acid and the added water were used in the following levels.

| | Added water | Methane sulfonic acid | |
|---|---|---|---|
| Example | g | g | mole (s) |
| 4 | 36.45 | 61.85 | 0.644 |
| 5 | none | 61.85 | 0.644 |
| 6 | 40.4 | 42.33 | 0.441 |
| 7 | 58.07 | 15.46 | 0.161 |
| 8 | 58.07 | 30.92 | 0.322 |

The reactants were added in the sequence described in Example 1. The formaldehyde was added starting at 105° C. over a period of 3 hours, Example 4, or 1.5 hours, Examples 5-8. The preparations of these Examples were conducted under continuous distillation of water, at the reaction temperature, thereby also eliminating a minimal amount of non-reacted formaldehyde. The reaction products were analyzed as in Example 1. The analytical results were as follows.

| Example | %-ATMP | %-Phosphorous acid | %-N-MeIBMPA |
|---|---|---|---|
| 4 | 69.4 | 18.6 | 2.7 |
| 5 | 74.6 | 13.3 | 2.6 |
| 6 | 67.9 | 20.4 | 3.5 |
| 7 | 64.6 | 18.1 | 8.4 |
| 8 | 67.7 | 20.4 | 3.9 |

The results illustrate the unusually significant benefits attached to the inventive technology, in particular, the high yields of aminopolyalkylene phosphonic acids formed in a short one-step reaction cycle under substantial exclusion of negatives attached to the state-of-the-art hydrochloric acid technology. It is particularly noteworthy that the distillate can be recycled/used without an additional purification step as is required in the presence of hydrochloric acid. Particular attention is also drawn to the substantial absence of methylchloride, especially in the gaseous by-products.

Additional aminopolyalkylene phosphonic acid preparations were carried out as described for Examples 4-8, except as specifically recited below. The listed ingredients were used, in Examples 9, 11-13, in identical levels as follows.

| Reactant | g | mole (s) |
|---|---|---|
| Phosphorous acid | 452.03 | 5.5125 |
| Ammonia (25% solution) | 122.4 | 1.8 |
| Formaldehyde (36.6% solution) | 464.71 | 5.67 |

The levels and species of catalyst and added water were selected as follows.

| | Catalyst | | | Added Water |
|---|---|---|---|---|
| Example | Species | g | mole (s) | g |
| 9 | $CH_3SO_3H$ | 278.2 | 2.899 | none |
| 11 | $CH_3SO_3H$ | 278.2 | 2.899 | none |
| 12 | idem | 278.2 | 2.899 | none |
| 13 | $H_2SO_4$ | 294.4 | 2.899 | none |

The reactants were added in the sequence of Example 1. The formaldehyde was added, starting from 105° C., over a period of:

1.5 hours—Examples 9 and 11, and 3 hours—Examples 12 and 13, under continuous distillation, at the reaction temperature. The reaction products, analyzed in accordance with Example 1, contained the listed products in the stated levels.

| Example | %-ATMP | %-Phosphorous acid | %-N-MeIBMPA |
|---|---|---|---|
| 9 | 78.3 | 10.6 | 3.8 |
| 11 | 77.7 | 10.3 | 3.5 |
| 12 | 75.7 | 11.3 | 3.1 |
| 13 | 72.2 | 8.5 | 3.2 |

Aminopolymethylene phosphonic acids were prepared, in accordance with Example 1, having the following compositions.

| | Example | | |
|---|---|---|---|
| Reactant | 15 | 16 | 17 |
| Phosphorous-g | 100.45 | 452.05 | 301.35 |
| acid-mole | 1.225 | 5.5125 | 3.67 |
| Ammonia-g | 27.2 | 122.4 | 81.6 |
| (25% solution)-mole | 0.4 | 1.8 | 1.2 |
| Formaldehyde-g | 103.27 | 464.7 | 309.8 |
| (36.6% solution)-mole | 1.26 | 5.67 | 3.77 |
| Water added-g | 58.07 | none | none |

The levels and species of catalysts used were as follows.

| | Catalyst | | |
|---|---|---|---|
| Example | Species | g | mole (s) |
| 15 | $CF_3COOH$ | 45 | 0.3 |
| 16 | Oxalic acid | 260.9 | 2.899 |
| 17 | p-Toluene sulfonic acid | 332.41 | 1.93 |

The reactants were added in the sequence of Example 1. The formaldehyde was added starting from 105° C. over a period of:

3 hours—Examples 16 and 17; and 2 hours—Example 15.

under continuous distillation as in Examples 9, 10-13. The reaction products, analyzed as in Example 1, contained the following phosphonate components.

| Example | %-ATMP | %-Phosphorous acid | %-N-MeIBMPA |
|---------|--------|--------------------|-------------| 
| 15 | 65   | 21.9 | 4.9  |
| 16 | 57.3 | 17.7 | 14.1 |
| 17 | 70.7 | 16.3 | 4.2  |

Ethylene diamino tetra(methylene phosphonic acid) (EDT-MPA), Examples 18, 20 and 21, were prepared by reacting, as set forth in Example 1, identical levels of the listed ingredients as follows.

| Reactant | g | mole(s) |
|----------|---|---------|
| Phosphorous acid | 426.4 | 5.2 |
| Ethylene diamine | 78.0 | 1.3 |
| Formaldehyde (36.6% solution) | 447.54 | 5.46 |

The catalyst—methane sulfonic acid alone or in combination with sulfuric acid—was used in the recited levels.

| Example | $CH_3SO_3H$ g/mole | $H_2SO_4$ g/mole |
|---------|--------------------|--------------------| 
| 18 | 291.86/3.04 | — |
| 20 | 91.24/0.95  | — |
| 21 | 91.24/0.95  | 19.6/0.2 |

The ingredients were added in accordance with Example 1. The formaldehyde was added, in Example 18, starting from 105° C. under distillation over a period of 4 hours. In Example 20, 90% of the ethylene diamine was added together with the formaldehyde starting from 105° C., under distillation over a period of 4 hours. In Example 21, 90% of the ethylene diamine was added, together with the formaldehyde starting from 105° C. under distillation, over a period of 4 hours and 20 minutes.

The reaction products, analyzed in accordance with Example 1, were found to contain:

| Example | %-EDTMPA | %-PP (z) | %-$H_3PO_3$ |
|---------|----------|----------|-------------| 
| 18 | 73.6 | 16.8 | 5.0 |
| 20 | 67.8 | 19.3 | 4.1 |
| 21 | 75.5 | 15.0 | 3.5 |

(z) = sum of ethylene diamino di- or tris-methylene phosphonic acids.

Diethylenetriamino penta(methylene phosphonic acids)—DTPMP—were prepared, Examples 22-24, by reacting, as set forth in Example 1, the listed ingredients in the stated proportions.

| Reactant | g/mole(s) |
|----------|-----------|
| Phosphorous acid | 426.40/5.2 |
| Diethylenetriamine | 107.30/1.04 |
| Formaldehyde (36.6% solution) | 447.54/5.46 |

The methane sulfonic acid catalyst was used in the specified levels.

| Example | g/mole(s) |
|---------|-----------|
| 22 (c) | 6.699/0.0697 |
| 23 | 306/3.18 |
| 24 | 155.75/1.62 |

(c) = comparative.

The reactants were added in the sequence of Example 1. The formaldehyde, in Example 22, was added, under distillation, starting from 105° C., over a period of 3 hours. Example 23 was identical to Example 22 except that the formaldehyde was added over a period of 2 hours and 40 minutes. Example 24 was prepared as Example 23, except that 10% of the diethylene triamine was charged with the other ingredients whereas 90% of the triamine was added together with the formaldehyde over a period of 4 hours and 20 minutes.

The reaction products were analyzed as in Example 1 and were found to contain the following compounds.

| Example acid | %-DTPMP | %-PP | %-Phosphorous |
|---------|---------|------|---------------|
| 22 | 0    | 0    | 1.8 |
| 23 | 58.8 | 28.8 | 4.9 |
| 24 | 59.4 | 24.9 | 4.9 |

The reaction product in comparative Example 22 contained 86% phosphoric acid but did not contain DTPMP.

Aminoalkylene phosphonic acids were prepared, Examples 25-30, by reacting, in a closed vessel under autogeneous pressure built up, the listed ingredient levels thereby using the operational sequence set forth in Example 1.

| Reactant | g/mole(s) | Example |
|----------|-----------|---------|
| Phosphorous acid | 42.6/0.52 | 25 |
| " | 85.28/1.04 | 26-30 |
| Diethylene triamine | 10.73/0.104 | 25 |
| " | 21.46/0.208 | 26-30 |
| Formaldehyde (36.6% solution) | 44.75/0.546 | 25 |
| " | 89.5/1.092 | 26-30 |

A methane sulfonic acid catalyst was used in the levels listed below.

| Example | Catalyst g/mole(s) |
|---------|--------------------|
| 25 | 15.57/0.162 |
| 26 | 31.14/0.324 |
| 27 | 31.14/0.324 |
| 28 | 46.72/0.487 |
| 29 | 46.72/0.487 |
| 30 | 50.91/0.53 |

The reactants were entered as in Example 1. In Example 25, 10% of the diethylene triamine ingredient was added with the other ingredients whereas 90% of the triamino material was added together with the formaldehyde, starting from 115° C., over a period of 3 hours. The preparation of Example 26 is identical to the preparation of Example 25 except that the formaldehyde/triamine was added over a period of one hour and 30 minutes. In Example 27, 40% of the diethylene triamine was added with the other ingredients whereas 60% of the triamino ingredient was added together with the formaldehyde over a period of 30 minutes starting from 125° C. The operational sequence of Example 28 was identical to the procedure of Example 27 except that the formaldehyde-triamine ingredient was added over a period of 4 minutes. The preparation of Example 29 was identical to Example 28 except that the formaldehyde-triamine ingredient was added over a period of 30 minutes. The preparational sequence of Example 30 was identical to the sequence of Example 28 except that the formaldehyde-triamine ingredient was added over a period of 3 minutes.

The reaction products, analyzed as in Example 1, were found to contain the following components.

| Example | %-DTPMP | %-PP | %-H$_3$PO$_3$ |
|---|---|---|---|
| 25 | 30.2 | 24.5 | 28.0 |
| 26 | 56.3 | 22.8 | 7.2 |
| 27 | 58.3 | 24.5 | 4.8 |
| 28 | 66.0 | 21.2 | 3.9 |
| 29 | 57.5 | 24.2 | 5.4 |
| 30 | 63.8 | 21.7 | 4.0 |

EXAMPLE 31(c)

A comparative aminopolymethylene phosphonic acid compound was prepared by reacting, in accordance with Example 1, the listed ingredient quantities.

| Reactant | g/mole (s) |
|---|---|
| Phosphorous acid | 426.4/5.2 |
| Methane sulfonic acid | 6.4/0.066 |
| Ethylene diamine | 78.0/1.3 |
| Formaldehyde (36.6% solution) | 447.5/5.46 |

The formaldehyde was added, under distillation, starting from 105° C. over a period of 4 hours.

The reaction product, analyzed as in Example 1, contained 0.4%-EDTMPA, 3.7% phosphorous acid and 58.1% phosphoric acid.

EXAMPLE 32

An aminopolymethylene phosphonic acid compound was prepared by reacting, in a closed vessel under autogeneous pressure built up, the listed ingredients in the manner described in Example 1.

| Reactant | g/moles (s) |
|---|---|
| Phosphorous acid | 45.20/0.551 |
| Methane sulfonic acid | 13.48/0.140 |
| Ammonia (32% solution) | 9.56/0.18 |
| Formaldehyde (36.6% solution) | 46.47/0.567 |

10% of the ammonia was added together with the other ingredients whereas the remaining 90% of the ammonia was added together with the formaldehyde, starting from 105° C., over a period of 3 hours.

The reaction product analyzed as in Example 1 contained the following compounds

| %-ATMP | 55.3 |
|---|---|
| %-N-MeIBMPA | 4.6 |
| %-Phosphorous acid | 17.5 |

Additional aminopolymethylene phosphonic acids were prepared, Examples 33-46, by reacting, in a closed vessel under autogeneous pressure built up, the listed ingredients in the stated proportions, as set forth in Example 1.

| Reactant | g/mole (s) | Example |
|---|---|---|
| Phosphorous acid | 90.40/1.102 | all |
| Ammonia (32% solution) | 19.12/0.36 | all |
| Formaldehyde (36.6% solution) | 92.94/1.134 | all |
| Methane sulfonic acid | 26.96/0.281 | 33-44 |
| " | 29.38/0.306 | 45 |
| " | 14.99/0.153 | 46 |

The formaldehyde/ammonia additions in the individual Examples were as follows.

EXAMPLE 33

10% of the ammonia was added at the start and 90% was added with the formaldehyde over a period of 90 minutes starting from 115° C.;

EXAMPLE 34

As in Example 33, except that 40% of the ammonia was added at the start and the formaldehyde/ammonia reactant was added over a period of 30 minutes;

EXAMPLE 35

As in Example 34, except that the formaldehyde/ammonia was added starting from 120° C.;

EXAMPLE 36

As in Example 34 except that the formaldehyde/ammonia was added starting from 125° C.;

EXAMPLE 37

As in Example 33, except that the formaldehyde/ammonia was added starting from 115° C. over a period of 30 minutes;

EXAMPLE 38

As in Example 37, except that the formaldehyde/ammonia was added starting from 125° C.;

EXAMPLE 39

As in Example 38, except that the formaldehyde/ammonia was added over a period of 30 minutes starting from 120° C.;

EXAMPLE 40

As in Example 39, except that 30% of the ammonia was added at the start while the remaining 70% was added with the formaldehyde;

EXAMPLE 41

As in Example 37, except that, 70% of the ammonia was added at the start and 30% with the formaldehyde;

EXAMPLE 42

As in Example 41, except that the formaldehyde/ammonia was added starting from 120° C.;

EXAMPLE 43

As in Example 42, except that the formaldehyde/ammonia was added over a period of 3 minutes starting from 115° C.;

EXAMPLES 44-46

As in Example 43, except that the formaldehyde/ammonia was added starting from 125° C.
The reaction products, analyzed as in Example 1, contained the following phosphonate compounds.

| Example | %-ATMP | %-N-MeIBMPA | %-H$_3$PO$_3$ |
|---|---|---|---|
| 33 | 63.0 | 4.9 | 14.3 |
| 34 | 69.2 | 6.4 | 13.2 |
| 35 | 70.8 | 6.0 | 9.5 |
| 36 | 69.1 | 5.9 | 8.6 |
| 37 | 68.1 | 6.4 | 10.9 |
| 38 | 64.2 | 5.5 | 9.3 |
| 39 | 67.2 | 6.2 | 10.2 |
| 40 | 72.4 | 6.0 | 8.7 |
| 41 | 72.9 | 6.5 | 10.8 |
| 42 | 72.3 | 5.7 | 9.5 |
| 43 | 68.7 | 9.2 | 12.7 |
| 44 | 70.9 | 8.3 | 10.4 |
| 45 | 70.7 | 8.1 | 11.4 |
| 46 | 68.3 | 10.4 | 10.0 |

A series of aminopolymethylene phosphonic acid compounds, Examples 47-59, were prepared in a closed vessel under autogeneous pressure built up thereby using the method of Example 1 with specific changes as follows.

| Reactants | g/mole (s) | Examples |
|---|---|---|
| Phosphorous acid | 90.40/1.102 | 47-53, 56 |
| " | 67.80/0.827 | 54, 55, 57 |
| " | 88.56/1.08 | 58, 59 |
| Ammonia (32% solution) | 19.12/0.36 | 47-53, 56, 58, 59 |
| " | 14.34/0.27 | 54, 55, 57 |
| Formaldehyde (36.6% solution) | 92.94/1.134 | 47-53, 56, 58, 59 |
| " | 69.70/0.85 | 54, 55, 57 |

The acid catalyst species were used in the listed proportions.

| Acid catalyst | g/mole (s) | Examples |
|---|---|---|
| Methane sulfonic acid | 20.73/0.216 | 53 |
| " | 22.03/0.229 | 54 |
| " | 25.92/0.27 | 55 |
| " | 26.95/0.281 | 49-51, 56 |
| " | 24.19/0.252 | 52 |
| " | 2.64/0.028 | 59 |
| " | 34.56/0.36 | 58 |
| " | 31.10/0.344 | 57 |
| Malonic acid | 21.63/0.281 | 47 |
| Oxalic acid | 25.27/0.281 | 48 |

The operational sequence of the reaction was performed as set forth in Example 1, with modified conditions as follows.

EXAMPLES 47, 48

As in Example 1, except that 70% of the ammonia was present at the start whereas 30% of the ammonia was added together with the formaldehyde, starting from 125° C. over a period of 30 minutes.

EXAMPLES 51-55

As in Example 47, except that the formaldehyde/ammonia was added starting from 145° C. over a period of 3 minutes.

EXAMPLES 49, 50

As in Example 51, except that the formaldehyde/ammonia was added, starting from 135° C., Ex. 49., or 140° C., Ex. 50.

EXAMPLES 56, 57

As in Example 1, except that the formaldehyde was added in 3 minutes starting from 145° C.

EXAMPLE 58

As in Example 1, except that 70% of the H$_3$PO$_3$ was added with the formaldehyde, under mechanical stirring, starting from 125° C. over a period of 3 minutes.

EXAMPLE 59

As in Example 1 except that the formaldehyde was added under stirring starting from 125° C. over a period of 30 minutes.
The reaction products, analyzed as in Example 1, showed the presence of phosphonate compounds as follows.

| Example | %-ATMP | %-N-MeIBMPA | %-H$_3$PO$_3$ |
|---|---|---|---|
| 47 | 45.7 | 16.6 | 24.6 |
| 48 | 60.0 | 13.3 | 14.0 |
| 49 | 70.2 | 8.0 | 9.8 |
| 50 | 68.0 | 8.6 | 7.4 |
| 51 | 63.0 | 11.8 | 7.5 |
| 52 | 64.7 | 10.5 | 8.3 |
| 53 | 66.6 | 9.7 | 6.3 |
| 54 | 67.0 | 8.0 | 8.3 |
| 55 | 67.1 | 6.9 | 9.6 |
| 56 | 62.3 | 12.0 | 8.2 |
| 57 | 64.9 | 10.3 | 9.0 |
| 58 | 67.9 | 15.5 | 10.7 |
| 59 | 58.9 | 16.3 | 11.8 |

The malonic acid catalyst, as used in Example 47, can decompose, during the reaction at temperatures exceeding e.g. about 125° C., into acetic acid having a pKa of 4.75 and CO$_2$. Thus while the yield of phosphonic acid is on the marginally low side, this insufficiency primarily originates from the limited thermal stability of the malonic acid catalyst at the reaction temperature.

EDTM-phosphonic acid, Example 60, was prepared by reacting, in the sequence set forth in Example 1, the listed ingredients in the stated proportions.

| Reactant | g | mole (s) |
| --- | --- | --- |
| Phosphorous acid | 82 | 1 |
| Ethylene diamine | 15 | 0.25 |
| Water | 10 | |
| Formaldehyde (36.6% solution) | 86.05 | 1.05 |
| Methane sulfonic acid | 12 | 0.125 |

The reactants, including 20% of the amine, were charged at the start of the reaction. 80% of the amine, together with the formaldehyde, was added during the reaction, starting at 130° C., over a period of 30 minutes.

The reaction product, analyzed as set forth in Example 1, was found to contain the following compounds.

| Example | %-EDTMPA | %-PP | %-$H_3PO_3$ | %-$H_3PO_4$ |
| --- | --- | --- | --- | --- |
| 60 | 57.6 | 23.2 | 3.9 | 4.3 |

The result illustrates the significance of the essential acid catalyst parameter. It is also noteworthy that preferred acid catalyst levels effectively improve the conversion of phosphorous acid to phosphonic acid thereby simultaneously (and desirably) inhibiting the oxidation of phosphorous acid to phosphoric acid.

DTPMP product, Example 61—comparative, was made by reacting, as set forth in Example 1, the listed reactants in the recited levels.

| Reactant | g | mole (s) |
| --- | --- | --- |
| Phosphorous acid | 85.28 | 1.04 |
| Diethylene triamine | 21.46 | 0.208 |
| Water | 10 | |
| Formaldehyde (36.6% solution) | 89.5 | 1.092 |

The reactants, including 40% of the amine, were charged at the start of the reaction. 60% of the amine, together with the formaldehyde, was added, over a period of 30 minutes, during the reaction starting at 130° C.

The reaction product, analyzed as in Example 1, was found to contain the following compounds.

| Example N° | %-DTPMP | %-PP | %-$H_3PO_3$ | %-$H_3PO_4$ |
| --- | --- | --- | --- | --- |
| 61 (c) | 5.2 | 24.4 | 4.1 | 40.6 |

The data demonstrate the need for using the essential acid catalyst. Minimum levels, as claimed, of the acid catalyst are required for securing the formation of acceptable levels of the aminoalkylene phosphonic acids.

Additional aminotrimethylene phosphonic acid compounds, Examples 62-64, were prepared by reacting the listed ingredients in the stated proportions thereby applying the sequence set forth in Example 1.

| Reactant | g | mole (s) |
| --- | --- | --- |
| Phosphorous acid | 68.88 | 0.84 |
| Water | 10.0 | |
| Ammonia (32% solution) | 14.87 | 0.28 |
| Formaldehyde (36.6% solution) | 72.3 | 0.882 |

The acid catalyst was used in the following proportions.

| Catalyst | Example N° | g | mole (s) |
| --- | --- | --- | --- |
| Methanesulfonic acid | 62 | 2.016 | 0.021 |
| Methanesulfonic acid | 63 | 10.08 | 0.105 |
| Ortho-phthalic acid | 64 | 46.51 | 0.28 |

The reactants, except the formaldehyde, were added to the reactor at the start at room temperature. This reaction mixture was then heated to 125° C. at which temperature the gradual addition over a period of 30 minutes of the formaldehyde was started. The reaction was conducted in a closed vessel under autogeneous pressure built up.

The reaction products, analyzed thereby using the method of Example 1, showed that the following compounds were formed.

| Example | %-ATMP | %-N-MeIBMPA | %-$H_3PO_3$ | %-$H_3PO_4$ |
| --- | --- | --- | --- | --- |
| 62 | 54.5 | 18.4 | 12.7 | 7.4 |
| 63 | 67.4 | 9.5 | 11.4 | 3.1 |
| 64 | 53.7 | 17.6 | 13.0 | 7.0 |

The results demonstrate benefits attached to the claimed technology, in particular the high yields obtained during a short, compared to conventional manufacturing methods, cycle with the further observation that there is ample room for optimizing the method considering the fairly substantial levels of un-reacted phosphorous acid.

The invention claimed is:

1. A method for the manufacture of amino polyalkylene phosphonic acid in presence of not more than 2000 parts-per-million, expressed in relation to the phosphorous acid component (100%), of hydrohalogenic acid, whereby all the available N—H functions in 50% or more of the amine raw material are converted to the corresponding alkylene phosphonic acids, by reacting:

(a): phosphorous acid;

(b): an amine selected from the group consisting of ammonia, primary amines and polyamines; and (c): a formaldehyde;

in reactant ratios as follows:

(a):(b) of from 0.05:1 to 2:1;

(c):(b) of from 0.05:1 to 5:1; and (c):(a) of from 5:1 to 0.25:1;

wherein (a) and (c) stand for the number of moles to be used and (b) represents the number of moles multiplied by the number of N—H functions in the amine, in the presence of an acid catalyst having a pKa equal to or less than 3.1, said acid catalyst (d) being homogeneous with respect to the reaction medium and being used in reactant ratios as follows:

(b):(d) of from 40:1 to 1:5;

wherein (d) stands for the number of moles of catalyst multiplied by the number of available protons per mole of catalyst, followed by recovering the amino polyalkylene phosphonic acid formed in a manner known per sé.

2. The method in accordance with claim 1 wherein the reactant ratios are as follows:

(a):(b) of from 0.1:1 to 1.50:1;
(c):(b) of from 0.2:1 to 2:1; and
(c):(a) of from 3:1 to 0.5:1.

3. The method in accordance with claim 1 wherein the acid catalyst is used in a ratio (b):(d) in the range of from 20:1 to 1:3.

4. The method in accordance with claim 1 wherein the reaction is carried out at a temperature in the range of from 45° C. to 200° C.

5. The method in accordance with claim 1 wherein the acid catalyst is selected from the group of sulfuric acid, sulfurous acid, trifluoroacetic acid, trifluoromethane sulfonic acid, methane sulfonic acid, oxalic acid, malonic acid, p-toluene sulfonic acid and naphthalene sulfonic acid, and mixtures thereof.

6. The method in accordance with claim 1 wherein the reactant ratios are as follows: (a):(b) of from 0.4:1 to 1.0:1.0; (c):(b) of from 0.4:1 to 1.5:1; and (c):(a) of from 2:1 to 1.0:1.

7. The method in accordance with claim 1 wherein the acid catalyst is used in a ratio (b):(d) in the range of from 10:1 to 1:2.

8. The method in accordance with claim 1 wherein the reaction is carried out at a temperature in the range of from 70° C. to 150° C. combined with an approach selected from:

conducting the reaction under ambient pressure with or without distillation of water and non-reacted formaldehyde;

in a closed vessel under autogeneous pressure built up;

in a combined distillation and pressure arrangement whereby the reaction vessel containing the reactant mixture is kept under ambient pressure at the reaction temperature followed by circulating the reaction mixture through a reactor operated under autogeneous pressure built up thereby gradually adding the formaldehyde and other selected reactants in accordance with needs; and a continuous process arrangement, possibly under autogeneous pressure built up, whereby the reactants are continuously injected into the reaction mixture and the phosphonic acid reaction product is withdrawn on a continuous basis.

9. The method in accordance with claim 1 wherein the amine is selected from the group of:

ammonia;

primary amines containing individual hydrocarbon groups having from 1 to 100 carbon atoms, said hydrocarbon moieties being represented by straight or branched linear alkyl moieties or cyclic alkyl moieties or aromatic or polyaromatic moieties or combinations thereof;

polyamines; and primary amines or polyamines containing alkoxylated or thioalkoxylated radicals and/or functional groups including trialkyl silyl, hydroxyl, carboxylic acid or sulfonic acid or esters of such acids or combinations thereof.

10. The method in accordance with claim 9 wherein the alkylamine is selected from methylamine, ethylamine, butylamine, octylamine, decylamine, dodecylamine, stearylamine, naphthylamine, benzylamine, aniline and cyclohexylamine.

11. The method in accordance with claim 1 wherein the acid catalyst has a pKa equal or inferior to 2.75.

12. The method in accordance with claim 1 wherein the phosphorous acid reactant is prepared, in a known manner, under substantial exclusion of halogen.

13. The method in accordance with claim 1 wherein the phosphorous acid is prepared, under substantial exclusion of halogen:

(i) by contacting elemental phosphorus with water at a temperature below 200° C. in the presence of a catalyst effective to promote oxidation of phosphorus by reaction with water; or (ii) by contacting P(V) species with a reducing agent such as hydrogen in the presence of a reducing catalyst; or (iii) by contacting a hydrolysis feed mixture comprising phosphite esters and phosphate esters with liquid water and steam to thereby hydrolyze the phosphite esters to phosphorous acid.

14. The method in accordance with claim 13 wherein the elemental phosphorus is tetraphosphorus.

15. The method in accordance with claim 9 wherein the polyamine is selected from the group of ethylene diamine, diethylene triamine, triethylene tetra-amine, di(propylene) ethylene tetra-amine, di(hexamethylene)triamine, hexamethylene diamine, polyethylene imine and polyallylamine.

16. The method in accordance with claim 1 wherein the phosphorous acid is prepared by reacting phosphorus trichloride with a reagent from the group of: a carboxylic acid; a sulfonic acid; and an alcohol followed by eliminating the chlorine containing products formed and the non-reacted raw materials by distillation or phase separation.

17. The method in accordance with claim 16 wherein chlorine containing products are eliminated to a level of 2000 parts-per-million (ppm) or smaller, expressed in relation to the level of the phosphorous acid component (100%).

18. The method in accordance with claim 1 wherein the phosphorous acid is prepared by hydrolyzing phosphorus trichloride followed by the substantial elimination of hydrochloric acid and other chloride intermediates originating from the hydrolysis.

19. The method in accordance with claim 18 wherein the hydrochloric acid and the chloride intermediates are eliminated to a level of 2000 ppm of phosphorous acid component (100%).

20. The method in accordance with claim 1 wherein the acid catalyst has a pKa inferior to 1.9.

21. The method in accordance with claim 9 wherein the individual hydrocarbon groups in the primary amines have from 1 to 50 carbon atoms.

* * * * *